United States Patent [19]
Simonnet et al.

[11] Patent Number: 6,126,948
[45] Date of Patent: Oct. 3, 2000

[54] STABLE OIL-IN-WATER EMULSION, PROCESS FOR ITS MANUFACTURE AND ITS USE IN THE COSMETIC AND DERMATOLOGICAL FIELDS

[75] Inventors: Jean-Thierry Simonnet, Paris; Danielle Le Verge, Vigneux sur Seine; Sylvie Legret, Chatillon; Isabelle Hansenne, Paris, all of France

[73] Assignee: L'Oreal, Paris, France

[21] Appl. No.: 09/041,664

[22] Filed: Mar. 13, 1998

[30] Foreign Application Priority Data

Mar. 13, 1997 [FR] France .................................. 97 03017

[51] Int. Cl.[7] ................................. A61K 7/00; A61K 7/42
[52] U.S. Cl. .............................. 424/401; 424/59; 424/60; 424/489; 424/501; 424/78.08; 514/844; 514/845; 514/846; 514/847; 514/848; 514/880; 514/881; 514/937; 514/938
[58] Field of Search ............................. 424/401, 59, 489, 424/501, 60, 78.08; 514/844, 845, 846, 847, 848, 880, 881, 937, 938

[56] References Cited

U.S. PATENT DOCUMENTS

| | | | |
|---|---|---|---|
| 5,556,617 | 9/1996 | Ribier et al. | 424/78.08 |
| 5,637,291 | 6/1997 | Bara et al. | 424/59 |
| 5,843,509 | 12/1998 | Calvo Salve e tal. | 424/489 |

FOREIGN PATENT DOCUMENTS

| | | |
|---|---|---|
| 0 681 830 | 11/1995 | European Pat. Off. . |
| 0 692 237 | 1/1996 | European Pat. Off. . |
| 2 681 248 | 3/1993 | France . |
| 0 688 561 | 12/1995 | France . |

*Primary Examiner*—Michael A. Williamson
*Attorney, Agent, or Firm*—Oblon, Spivak, McClelland, Maier & Neustadt, P.C.

[57] ABSTRACT

A fine and stable emulsion of an oily phase in an aqueous phase containing ionic polymer particles, the oil globules of the emulsion having a mean size of at most 500 nm, a process for the stabilization of fluid emulsions, a process for the preparation of these emulsions and their use in the cosmetic and dermatological fields and more particularly as composition for anti-sun protection.

18 Claims, No Drawings

STABLE OIL-IN-WATER EMULSION, PROCESS FOR ITS MANUFACTURE AND ITS USE IN THE COSMETIC AND DERMATOLOGICAL FIELDS

BACKGROUND OF THE INVENTION

1. Field of the Invention

The invention relates to a fine and stable oil-in-water (O/W) emulsion containing ionic polymer particles and to its process of preparation. This emulsion can constitute a composition intended in particular for the topical treatment of the skin (body, face) and/or of the hair, in particular a cosmetic or dermatological composition, intended in particular for anti-sun protection. The invention also relates to the use of the emulsion according to the invention for the photochemical stabilization of chemical sunscreens and to the use of ionic polymer particles for the stabilization of a fluid oil-in-water emulsion.

2. Description of the Background

For various reasons relating in particular to their great comfort of use and to their freshness, cosmetic compositions, in particular those intended for the photoprotection of the skin against UV-A and UV-B radiation, known as anti-sun compositions, are generally provided in the form of an oil-in-water emulsion containing an oily phase dispersed homogeneously in an aqueous phase. In these conventional emulsions, which contain emulsifying (or surface-active) agents and optional cosmetic additives, the size of the globules constituting the fatty phase is generally greater than several microns. Such emulsions can have unsatisfactory cosmetic (oily feel) and physical (stability) properties.

Moreover, it is observed that, despite the presence of emulsifying (or surface-active) agents, some of these emulsions exhibit a lack of stability over time, a lack of stability which is reflected by the appearance of a separation phenomenon (phase separation) between the aqueous and oily phases of the emulsion. This instability is harmful to the storage of the emulsions.

Consequently, in order to avoid this undesirable phenomenon, it is often necessary to resort to so-called thickening agents which are then introduced into the emulsion, the main function of which is to create, within the aqueous phase, a gelled matrix which serves to set, within its three-dimensional network, the globules of the fatty phase, thus providing for mechanical maintenance of the entire emulsion. However, this addition of thickener limits the possible pharmaceutical dosage forms, excluding in particular very fluid compositions.

Now, there is an increasing search to prepare fluid compositions, in particular anti-sun compositions, more specifically with the aim of having available products which can easily evaporate, which products are often regarded by the user as easier to apply than creams.

Moreover, the presence of surfactants generally requires the emulsion to be manufactured with heating, which limits in particular the nature of the active agents to be introduced into the emulsion. In particular, this process excludes the use of heat-sensitive active agents. Consequently, attempts have been made, in addition to searching for fluidity, to dispense with surfactants.

It is known, from EP-A-0,692,237, to stabilize O/W emulsions with hollow particles of non-ionic polymer. However, hollow particles of this type, of non-ionic nature and with a size of the order of a micron, do not make it possible to obtain very fine emulsions, the oil droplets of which have a size of less than 500 nm. In addition, the particles described in this document require the presence of a gelling agent in order to improve the stability of the dispersion and do not make it possible to obtain very fluid emulsions.

Moreover, FR-A-2,681,248 describes compositions containing nanoparticles encapsulating an oil. Such particles can be incorporated in a preprepared emulsion but cannot participate in the preparation and in the stabilization of an emulsion because they can open during excessively vigorous agitation. In particular, they are not suitable for the production of very fine emulsions, that is to say containing oil droplets with a size of less than 500 nm.

In addition, the nanoparticles described in this document form capsules containing an oil and have the function of protecting the oil in the composition in order to release it only when applied to the skin. The oil therein is completely encapsulated in the film of the nanoparticles. The aim of the present invention is to obtain an emulsion where very fine oil droplets are not encapsulated but are distributed in the aqueous phase.

SUMMARY OF THE INVENTION

In the emulsion according to the invention, the polymer particles are at the interface of the water and of the oil droplets in particulate form, without forming a continuous closed capsule surrounding each oil droplet, as is the case with the nanoparticles. Furthermore, the aim is entirely different, since the function of the polymeric nanoparticles in the prior art is to protect the oil in the composition in order to release it when applied to the skin, whereas the function of the polymer particles in the invention is to make possible the stabilization of the emulsion, even without addition of surfactant.

It has been discovered, unexpectedly, that the use of ionic polymer particles makes it possible to obtain stable fluid emulsions which do not exhibit the disadvantages of the emulsions of the prior art and which contain oil globules having a mean size of less than 500 nanometers (nm).

The subject of the present invention is thus an emulsion of an oily phase in an aqueous phase containing oil globules having a diameter of less than 500 nanometers, characterized in that it contains ionic polymer particles and in that the ratio of the amount of polymer particles to the amount of oily phase ranges from about ⅕ to about ¹⁄₄₀.

DETAILED DESCRIPTION OF THE INVENTION

"Ionic polymer" is understood to mean both a homopolymer and a copolymer. The aim of the polymers is in particular to disperse the oily phase in the aqueous phase.

The emulsions according to the invention in particular exhibit the advantage of being able to be very fluid while exhibiting very good stability, even in the absence of a gelling agent.

In addition to the abovementioned advantages (fluidity, stability), the use of the polymer particles as dispersant makes it possible to carry out the stage of dispersion of the oily phase in the aqueous phase under cold conditions, which is simpler and less expensive than conventional processes generally carried out with heating, when surfactants are used. Manufacture under cold conditions makes it possible, for example, to introduce heat-sensitive active agents without risk of degradation of these active agents.

The emulsion of the invention is advantageously devoid of surfactant. Thus, because of the absence of surfactant, this emulsion exhibits the advantage of not being irritating to particularly sensitive skin.

Moreover, the emulsion thus obtained is very fine and exhibits particularly satisfactory sensorial qualities. The mean size of the globules constituting the oily phase is less than 500 nm and it preferably ranges from 150 nm to 300 nm.

The emulsion according to the invention can be very fluid, which means that it can exhibit a viscosity of less than 15,000 cPs (i.e. 15 Pa.s), more preferably still of less than 5000 cPs (i.e. 5 Pa.s) (measured on a Brookfield RVT model DV2 viscometer at 0.5 revolution/minute and with a No. 5 rotor).

Generally, the particles which can be used in the invention can be prepared from an ionic polymer, from a mixture of ionic polymers or from a mixture of at least one ionic polymer and of at least one non- ionic polymer. These polymers must be non-toxic old non-irritating to the skin. In addition, they must be able to disperse in water in the particulate form.

The ionic polymer can be cationic or anionic. It is preferably an anionic polymer. The anionic polymers which can be used in the invention are, for example, polymers of isophthalic acid or of sulphoisophthalic acid and in particular the phthalate/sulphoisophthalate/glycol (for example, diethylene glycol/phthalate/isophthalate/1,4-cyclohexanedimethanol) copolymers sold under the names "Eastman AQ polymer" (AQ35S, AQ38S, AQ55S or AQ48 Ultra) by the company Eastman Chemical.

Advantageously, the ionic polymer particles used according to the invention have a particle size ranging from about 10 to about 400 nm and preferably ranging from 20 to 200 nm, depending on the nature of the ionic polymer.

The particles of these polymers can be used as is or in dispersion in water.

In the emulsions of the invention, use may be made of an amount of polymer particles ranging from about 0.1 to about 10%, preferably from 0.5 to 5% and more preferably from 1 to 2% of the total weight of the composition.

The ratio by weight of the polymer particles to the oily phase advantageously ranges from about 1/5 to about 1/40, and preferably from 1/10 to 1/20. Such a ratio makes it possible to obtain a fluid oil dispersion which is fine, that is to say having globules with a particle size of less than 500 nm, and completely stable.

Another object of the invention is the use of ionic polymer particles for the stabilization of an oil-in-water fluid emulsion containing oil globules having a mean size of at most 500 nm.

The emulsion according to the invention can be used in all fields using this type of pharmaceutical dosage form and in particular in the cosmetic and dermatological fields. When it constitutes a cosmetic and/or dermatological composition, it advantageously contains, in addition, a physiologically acceptable medium. Physiologically acceptable is understood to mean a medium compatible with the skin, the mucous membranes, the nails and the hair.

The emulsions which are the subject of the invention find their application in a great number of cosmetic and/or dermatological treatments of the skin, mucous membranes and hair, including the scalp, in particular for the protection, care, cleansing and making up of the skin and mucous membranes, for the protection and care of the hair and for the therapeutic treatment of the skin, hair and mucous membranes and more especially of the lips.

The emulsions according to the invention can, for example, be used in care or cleansing products for the face in the form of creams or milks or as make-up products (skin and lips) by incorporation of fillers, pigments or dyes. According to a specific embodiment of the invention, the emulsion contains a sunscreen and more particularly constitutes an anti-sun composition intended for the protection of the skin, mucous membranes and/or hair against ultraviolet radiation, in particular against solar radiation.

Consequently, a further object of the invention is the cosmetic use of the emulsion as defined above for the treatment of the skin, mucous membranes and/or hair and/or for the protection of the skin, mucous membranes and/or hair against ultraviolet radiation, in particular solar radiation.

Another object of the invention is the use of the emulsion as defined above for the manufacture of a dermatological composition intended for the treatment of the skin, mucous membranes and/or hair and/or for the protection of the skin, mucous membranes and/or hair against ultraviolet radiation, in particular solar radiation.

A further object of the invention is a treatment process for protecting the skin, mucous membranes and/or hair against ultraviolet radiation, in particular solar radiation, characterized in that it consists in applying an effective amount of the anti-sun composition as defined above to the skin, mucous membranes and/or hair.

The anti-sun compositions contain one or more sunscreens which are active in the UV-A and/or UV-B. These screening agents can be hydrophilic or lipophilic chemical screening agents or can be pigments. By way of examples, the chemical screening agents can be chosen from 2-phenylbenzimidazole-5-sulphonic acid and its salts, cinnamic derivatives, such as, for example, 2-ethylhexyl p-methoxycinnamate, salicylic derivatives, such as, for example, 2-ethylhexyl salicylate and homomethyl salicylate, camphor derivatives, such as, for example, 3-(4-methylbenzylidene)camphor or camphorsulphonic acid-(1, 4-divinylbenzene), triazine derivatives, such as 2,4,6-tris[p-(2-ethylhexyloxy-carbony)anilino]-1 ,3,5-triazine, benzophenone derivatives, such as 2-hydroxy-4-methoxybenzophenone, dibenzoylmethane derivatives, such as 4-tert-butyl-4'-methoxydibenzoylmethane, β,β-diphenylacrylate derivatives, such as 2-ethylhexyl α-cyano-β,β-diphenylacrylate or octocrylene, p-aminobenzoic acid derivatives, such as, for example, octyl para-dimethylaminobenzoate, or menthyl anthranilate. Mention may also be made, as screening agents, of the screening polymers and screening silicones described in Application WO-A-93/04665 and in particular benzotriazole silicones.

Other examples of organic screening agents are disclosed in Patent Application EP-A-0,487,404.

When the anti-sun compositions of the invention contain pigments, the latter can be pigments or nanopigments (mean size of the primary particles: generally between 5 nm and 100 nm, preferably between 10 and 50 nm) of metal oxides, which are coated or non-coated, such as, for example, nanopigments of titanium oxide (amorphous or crystallized in the rutile and/or anatase form), iron oxide, zinc oxide, zirconium oxide or cerium oxide which are all photoprotective agents well known per se which act by physically blocking (reflection and/or scattering) UV radiation. Conventional coating agents are, for example, alumina and/or aluminum stearate. Such coated or non-coated metal oxide nanopigments are disclosed in particular in EP-A-0,5 18,772 and EP-A-0,5 18,773.

These chemical screening agents and/or pigments can optionally be present in compositions other than anti-sun compositions, when a degree of anti-sun protection is desired.

Moreover, it has also been found, unexpectedly, that the emulsions according to the invention make possible photochemical stabilization of chemical sunscreens. A further object of the invention is consequently the use of the emulsion as defined above for the photochemical stabilization of chemical sunscreens.

The nature of the oily phase taking part in the composition of the emulsions according to the invention is not critical and it can thus be composed of all the fatty substances and in particular oils conventionally used in the cosmetic and dermatological fields.

Mention may in particular be made, among oils which can be used in the emulsion of the invention, of, for example, vegetable oils (jojoba or avocado oil), mineral oils (liquid petrolatum), synthetic oils (ethylhexyl palmitate or isopropyl myristate), silicone oils (cyclomethicone) and fluorinated oils. The other fatty substances capable of being present in the oily phase can be, for example, fatty acids, fatty alcohols and waxes (liquid jojoba wax).

The oily phase of the emulsion can be present in an amount of from about 0.1 to about 45% and preferably from 5 to 30% of the total weight of the emulsion.

In addition, in a known way, the emulsions of the invention can contain, besides the sunscreens and the pigments mentioned above, adjuvants usual in the cosmetic or dermatological field, such as active agents, these being hydrophilic or lipophilic, preservatives, antioxidants, fragrances, fillers, colouring materials and lipid vesicles. These adjuvants are used in the proportions usual in the cosmetic or dermatological field, for example from about 0.01 to about 20% of the total weight of the emulsion, and they are, depending on their nature, introduced in the aqueous phase or in the oily phase of the emulsion or alternatively in vesicles. These adjuvants and their concentrations must be such that they do not modify the property desired for the emulsion.

If it is desired to obtain a less fluid emulsion, it is possible to add thereto one or more gelling agents, such as clays, polysaccharide gums (xanthan gum), carboxyvinyl polymers or carbomers. These gelling agents are used at concentrations ranging from about 0.1 to about 10%, preferably from 0.1 to 5% and more preferably from 0.1 to 3% of the total weight of the composition.

The emulsions of the invention can optionally be devoid of solvent. This also favours an only slightly aggressive and non-irritating emulsion suitable for use by people with sensitive skin. However, if necessary, they can contain a solvent, in particular a lower alcohol containing from one to six carbon atoms, more particularly ethanol. The amount of solvent can range up to 30% of the total weight of the composition.

The emulsions according to the invention can be prepared by any appropriate means including a stage of homogenization under pressure. According to a preferred embodiment, the preparation is carried out in two stages.

A further object of the invention is consequently a process for the manufacture of the emulsion which consists, in a first stage, in mixing the aqueous phase, the oily phase and the polymer particles with stirring and, in a second stage, in subjecting the mixture obtained to a homogenization based on the cavitation principle.

In the first stage, the mixture is stirred conventionally, for example in a homogenizer rotating at a speed of between 500 and 5000 revolutions/min, for a time of between 10 and 60 min approximately at a temperature of between 20 and 95° C. approximately.

The homogenization based on the cavitation principle of the second stage is a key stage in the process according to the invention. This homogenization results from the cavitation phenomenon created and maintained within the mixture, then in the liquid form, in moving at a linear velocity of at least 100 m/s.

This homogenization can be carried out by use of a high-pressure homogenizer operating under a pressure ranging from 100 to 1000 bar approximately, preferably from 400 to 700 bar. The principle of use of this type of homogenizer is well known to a person skilled in the art. The homogenization is carried out at ambient temperature by successive passes, generally from 2 to 10 passes, under the pressure used, the mixture being brought back to ambient temperature between each pass.

The homogenization can also be obtained under the effect of ultrasound or alternatively by use of homogenizers equipped with a head of rotor/stator type.

Having generally described this invention, a further understanding can be obtained by reference to certain specific examples which are provided herein for purposes of illustration only and are not intended to be limiting unless otherwise specified.

In these examples, the percentages are given by weight.

EXAMPLE 1

Fluid Anti-Sun Composition

| Phase A | |
|---|---|
| AQ38S (Eastman Chemical) | 2% |
| Glycerol | 5% |
| Preservatives | 1.2% |
| Sequestering agent | 0.1% |
| Demineralized water | q.s. for 100% |
| Phase B | |
| Octocrylene | 10% |
| 4-tert-Butyl-4'-methoxydibenzoylmethane (Parsol 1789, sold by the company Givaudan) | 2% |
| Cyclomethicone | 4% |
| Liquid jojoba wax (Flora Tech) | 4% |

Procedure: The constituents of phase A are mixed, the mixture is heated at 70° C. with magnetic stirring until the polymer has completely dispersed and then the solution is cooled to ambient temperature. Moreover, phase B is prepared.

Phase A is introduced into phase B with vigorous stirring. The emulsion is homogenized under a pressure of 600 bar (2 to 4 passes), the emulsion being brought back to ambient temperature between each pass.

A fluid emulsion is obtained which is capable of protecting the skin against solar radiation.

EXAMPLE 2
Anti-Sun Composition

| Phase A | |
|---|---|
| AQ38S (Eastman Chemical) | 2% |
| Glycerol | 5% |
| Preservatives | 1.2% |
| Sequestering agent | 0.1% |
| Demineralized water | 34.7% |
| Phase B | |
| Octocrylene | 10% |
| 4-tert-Butyl-4'-methoxydibenzoylmethane (Parsol 1789, sold by the company Givaudan) | 2% |
| Cyclomethicone | 4% |
| Liquid jojoba wax (Flora Tech) | 4% |
| Phase C | |
| Xanthan gum | 0.5% |
| Demineralized water | q.s. for 100% |

The procedure is identical to that in Example 1, phase C being added after mixing phases A and B and before passing through the homogenizer.

EXAMPLE 3 and 4
Anti-Sun Compositions

Examples 3 and 4 correspond to emulsions, respectively analogous to those in Examples 1 and 2, containing 10% of octocrylene.

The photostability of octocrylene in the compositions of these examples was studied, in comparison with a conventional composition (screening agent in rapeseed oil) containing the same amount of screening agent, in the following test:

For each of these compositions, a determination was carried out of the percentage of residual octocrylene after irradiation by UV radiation according to the following protocol: for each formula, four control samples and four test samples were prepared. 16 mg of formula were deposited on depolished PMMA (poly(methyl methacrylate)) plates, which had been rinsed beforehand with water and then dried, and the formula was spread over an area of 2×4 cm². All the plates were subsequently allowed to stand for half an hour in the dark. The plates (Heraeus Suntest CPS) were then irradiated for 4 hours and 5 minutes, the control plates being stored in the dark during the period of irradiation of the other plates.

The samples were subsequently quantitatively determined in the following way: the screening agent was extracted by immersing each plate in 50 g of isopropanol in order to dissolve the screening agent. The plates and the solvent containing the screening agent were subsequently treated with ultrasound for 5 minutes in order to provide efficient agitation. The total concentration of residual screening agent was quantitatively determined with a spectrophotometer.

The results, as percentage of residual screening agent, are recorded in the following Table I:

TABLE I

| Composition | % of residual octocrylene |
|---|---|
| Conventional composition | 92% |
| Example 3 | 99.6% |
| Example 4 | 99.7% |

These results clearly show that the photostability of octocrylene is enhanced in the emulsions of the invention.

EXAMPLE 5
Moisturizing Care Product

| Phase A | |
|---|---|
| AQ38S (Eastman Chemical) | 2% |
| Glycerol | 5% |
| Demineralized water | q.s. for 100% |
| Phase B | |
| Avocado oil | 7% |
| Jojoba oil | 7% |
| Preservative | 0.1% |
| Cyclomethicone | 6% |

The procedure is identical to that in Example 1.

A white, very fluid emulsion is obtained in which the mean size of oil globules is less than 350 nm.

EXAMPLE 6
Moisturizing Care Product

| Phase A | |
|---|---|
| AQ55S (Eastman Chemical) | 2% |
| Glycerol | 5% |
| Preservatives | 1% |
| Demineralized water | 35% |
| Phase B | |
| Avocado oil | 7% |
| Jojoba oil | 7% |
| Cyclomethicone | 6% |
| Phase C | |
| Xanthan gum | 0.5% |
| Demineralized water | q.s. for 100% |

The procedure is identical to that in Example 2.

A very fine emulsion is obtained in which the mean size of oil globules is of the order of 230 nm.

EXAMPLE 7
After-Sun Fluid

| Phase A | |
|---|---|
| AQ48 Ultra (Eastman Chemical) | 2% |
| Glycerol | 5% |
| Preservatives | 1% |
| Demineralized water | q.s. for 100% |
| Phase B | |
| Jojoba oil | 10% |
| Cyclomethicone | 10% |
| α-Bisabolol (soothing agent) | 0.25% |

The procedure is the same as that in Example 1. A very fluid emulsion is obtained in which the mean size of oil globules is of the order of 225 nm.

EXAMPLE 8
Make-Up Removal Milk

| Phase A | |
|---|---|
| AQ38S (Eastman Chemical) | 2% |
| Glycerol | 5% |
| Preservatives | 1% |
| Demineralized water | 35% |
| Phase B | |
| Ethylhexyl palmitate | 14% |
| Isopropyl myristate | 10% |
| Cyclomethicone | 6% |
| Phase C | |
| Xanthan gum | 0.3% |
| Demineralized water | q.s. for 100% |

The procedure is the same as that in Example 2. A very fluid emulsion is obtained in which the mean size of oil globules is of the order of 250 nm. This emulsion has very good make-up removal properties.

The disclosure of France priority patent application 97-03017, filed Mar. 13, 1997, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed is:

1. An emulsion of an oily phase in an aqueous phase containing oil globules having a diameter of less than 500 nanometers, wherein said emulsion contains ionic polymer particles in a ratio by weight of the polymer particles to the oily phase of from about 1/5 to about 1/40, and wherein said oil globules are not encapsulated in said polymer particles.

2. The emulsion according to claim 1, which is devoid of surfactant.

3. The emulsion according to claim 1, wherein the ionic polymer is an anionic or cationic polymer, or a mixture thereof, or a mixture of at least one ionic polymer and at least one non-ionic polymer.

4. The emulsion according to claim 1, wherein the ionic polymer is an anionic polymer.

5. The emulsion according to claim 4, wherein the ionic polymer is a isophthalic acid and/or of sulphoisophthalic acid.

6. The emulsion according to claim 1, wherein the particles have a particle size ranging from about 10 to about 400 nanometers.

7. The emulsion according to claim 1, wherein the particles are present in an amount of from about 0.1 to about 10% of the total weight of the emulsion.

8. The emulsion according to claim 1, wherein the ratio by weight of the polymer particles to the oily phase ranges from 1/10 to 1/20.

9. The emulsion according to claim 1, wherein the oily phase is present in an amount of from about 0.1 to about 45% of the total weight of the emulsion.

10. The emulsion according to claim 1, additionally containing at least one cosmetic and/or dermatological ingredient.

11. The emulsion according to claim 1, additionally containing at least one additive selected from the group consisting of hydrophilic active agents, lipophilic active agents, preservatives, antioxidants, fragrances, fillers, sunscreens, pigments, colouring materials and lipid vesicles.

12. Anti-sun composition comprising the emulsion according to claim 1 and at least one sunscreen agent.

13. Anti-sun composition according to claim 12, wherein the sunscreen agent is a chemical screening agent.

14. Anti-sun composition according to claim 13, wherein the sunscreen agent is selected from the group consisting of 2-phenylbenzimidazole-5-sulphonic acid and its salts, cinnamic derivatives, salicylic derivatives, camphor derivatives, triazine derivatives, benzophenone derivatives, dibenzoylmethane derivatives, β,β-diphenylacrylate derivatives, p-aminobenzoic acid derivatives, menthyl anthranilate, screening polymers and screening silicones.

15. Anti-sun composition according to claim 12, wherein the sunscreen agent is a pigment or a nanopigment.

16. A process for treatment of the skin, mucous membranes and/or hair and/or for the protection of the skin, mucous membranes and/or hair against ultraviolet radiation comprising applying an effective amount of the composition of claim 12 to said skin, membranes and/or hair.

17. A process for the manufacture of an emulsion as defined in claim 1 which comprises, in a first stage, mixing the aqueous phase, the oily phase and the polymer particles with stirring and, in a second stage, subjecting the mixture obtained to a homogenization based on the cavitation principle.

18. The process according to claim 17, wherein, in the second stage, the homogenization is carried out under a pressure ranging from 400 to 700 bar.

* * * * *